US010292397B2

(12) United States Patent
Boston

(10) Patent No.: US 10,292,397 B2
(45) Date of Patent: May 21, 2019

(54) USE OF PROTEINS TO CONTROL MOLLUSCS

(71) Applicant: Marrone Bio Innovations, Inc., Davis, CA (US)

(72) Inventor: Matt Boston, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 4 days.

(21) Appl. No.: 15/577,442

(22) PCT Filed: May 24, 2016

(86) PCT No.: PCT/US2016/033945
§ 371 (c)(1),
(2) Date: Nov. 28, 2017

(87) PCT Pub. No.: WO2016/191430
PCT Pub. Date: Dec. 1, 2016

(65) Prior Publication Data
US 2018/0139968 A1    May 24, 2018

Related U.S. Application Data

(60) Provisional application No. 62/167,860, filed on May 28, 2015.

(51) Int. Cl.
| | |
|---|---|
| *C02F 1/50* | (2006.01) |
| *C02F 3/32* | (2006.01) |
| *A01N 63/02* | (2006.01) |
| *A01N 37/46* | (2006.01) |
| *C09D 5/16* | (2006.01) |
| *C02F 103/00* | (2006.01) |

(52) U.S. Cl.
CPC ............ *A01N 63/02* (2013.01); *A01N 37/46* (2013.01); *C02F 1/50* (2013.01); *C02F 3/327* (2013.01); *C09D 5/1625* (2013.01); *C02F 2103/007* (2013.01); *Y02W 10/18* (2015.05)

(58) Field of Classification Search
None
See application file for complete search history.

(56) References Cited

U.S. PATENT DOCUMENTS

2007/0020625 A1  1/2007 Duchaud et al.
2013/0196013 A1  8/2013 Asolkar et al.

FOREIGN PATENT DOCUMENTS

EP     0598746 B1     9/1996
WO   2014116378 A1    7/2014

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Database NCBI Accession No. WP_011061271.1; Apr. 11, 2014, pp. 1-3.
International Search Report and Written Opinion for PCT/US2016/033945 dated Sep. 7, 2016.
Molloy et al., "Pseudomonas fluorescent strain CL145A—A biopesticide for the control of zebra and quagga mussels (Bivalvia: Dreissenidae)"; Journal of Invertebrate Pathology, vol. 113, Pub Jan. 5, 2013, pp. 104-114.
European Extended Search Report, App. No. 16800641.9, dated Oct. 18, 2018, pp. 1-8.
Guglielmo Lucchese, et al.; "Flow a single amino acid change may alter the immunological information of a peptide"; Frontiers in Bioscience E4, pp. 1843-1852, Jan. 1, 2012.
Ian T. Paulsen et al.; "Complete genome sequence of the plant commensal Pseudomonas fluorescent Pf-5"; Nature Biotechnology, vol. 23, No. 7, Jul. 2005, pp. 873-878.
Paulsen, I.T.; "Pseudomonas protegens Pf-5, complete genome"; GenBank, Nat. Biotechnol. 23 (7), 873-878 (2005).

* cited by examiner

*Primary Examiner* — Brian Gangle
(74) *Attorney, Agent, or Firm* — Chainey Singleton; Ying-Horng Liu

(57) ABSTRACT

The present disclosure includes proteins toxic to Zebra mussels, its method of production, and uses thereof. The protein was isolated from whole cell broth of *Pseudomonas protegens* CL145A via anion exchange chromatographic fractionation. The protein was found to be a secondary metabolite with highest expression at the fermentative production harvest stage.

5 Claims, 4 Drawing Sheets

Specification includes a Sequence Listing.

SEQUENCE LISTING

<160> NUMBER OF SEQ ID NOS: 1

<210> SEQ ID NO 1
<211> LENGTH: 3003
<212> TYPE: PRT
<213> ORGANISM: Pseudomonas protegens CL145A

<400> SEQUENCE: 1

```
Met Ala Phe Met Ser Lys Asp Phe Thr Arg Leu Leu Asn Thr Leu Ile
1               5                   10                  15

Asp Gln Gln Ile Lys Thr Ala Gly Arg Gln Thr Glu Trp Phe Asn Met
            20                  25                  30

Ser Ala Asp Glu Arg Ala Ala Tyr Ile Gly Gln Val Gly Glu Arg Leu
        35                  40                  45

Leu Glu Met Gln Gln Ser Thr Leu Ser Val Leu Ala Ala Gln His Tyr
    50                  55                  60

Gln Met Gln Asp Asn Pro Val Ser Val Gly Asp Gln Leu Gln Val Leu
65                  70                  75                  80

Gln Gln Arg Arg Lys Glu Met Lys Ala Ile Ala Asp Thr Pro Ala Thr
                85                  90                  95

Ile Ala Tyr Lys Gln Gln Leu Asp Arg Asp Ile Leu Leu Tyr Ser Arg
            100                 105                 110

Gln Asp Thr Ala Ile Ser His Tyr Asp Ser Thr Trp Asn Lys Ala Leu
        115                 120                 125

Arg Leu Leu Ser Pro Gly Gly Ala Lys Ala Glu Val Leu Gln Ala Asp
    130                 135                 140

Ala Pro Ala Lys Gln Lys Glu Leu Lys Gly Arg Ile Asn Arg Leu Glu
145                 150                 155                 160

Lys His Leu Ser Leu Gln Val Ala Asp Ser Thr Phe Ser Gln Thr Tyr
                165                 170                 175

Val Thr Leu Phe Ser Glu Leu Gln Ala Tyr Lys Glu Val Ser Thr Arg
            180                 185                 190

Tyr Asn Ala Trp Leu Lys Ala Ala Pro Gln Gln Ala Ala Ser Leu
        195                 200                 205

Asp Ala Leu Ala Lys Pro Pro Arg Ala Ser Asp Glu Leu Pro Val Asn
    210                 215                 220
```

```
Leu Ser Leu Leu Met Met Glu Glu Arg Pro Gly Tyr Ile Arg Met Asn
225                 230                 235                 240

Val Ala Leu Val Asn Ala Ser Thr Asp Gly Arg Phe Lys Asp Phe Tyr
            245                 250                 255

Leu Glu His Gly Arg Leu Val Val Pro Thr Asp Gly Val Leu Asn Phe
        260                 265                 270

Ser Phe Gly Thr Ala Ala Arg Ser Leu Ala Trp Gln Gln Gln Tyr Arg
        275                 280                 285

Leu Lys Ser Glu Pro Pro Ser Met Arg Ser Pro Thr Tyr Ala Pro Ile
    290                 295                 300

Arg Ser Val Leu Val Lys Thr Gly Phe Val Glu Gln Tyr Phe Ala Asn
305                 310                 315                 320

His Leu Val Ser Glu Ser Leu Arg Glu Gly Phe Lys Ala Gln Val
                325                 330                 335

Leu Ser Asn Gly Arg Lys Leu Leu Thr Gly Val Asp Arg Lys Val
                340                 345                 350

Pro Asn Gln Val Gly Ile Gln Val Ser Gly Ser Pro Gly Thr Ser
        355                 360                 365

Val Thr Arg Glu Val Pro Leu Ala Gly Ala Leu Ser Glu Leu Ile Asn
    370                 375                 380

Gln Asn Ala Asp Ile Thr Ser Phe Gln Thr Leu Gly Val Glu Asp Tyr
385                 390                 395                 400

Arg Gln Asn Ser Tyr His Pro Asp Arg Asp Gly Leu Phe Val Asn Ile
                405                 410                 415

His Glu Leu Glu Arg Ser Val Gly Phe Ala Glu His Gln Tyr Leu Leu
                420                 425                 430

Glu Met Pro Gln Gly Asp Ala Tyr Arg Ser Ala Thr Pro Phe Ala Val
        435                 440                 445

Met Thr Val Glu Gly Asp Lys Val Ser Ser His Leu Ser Lys Ala
    450                 455                 460

Gln Thr Glu Thr Leu Tyr Gln Tyr Asn Ala Ala Phe Phe Glu Arg Leu
465                 470                 475                 480

Glu Gln Leu Arg Gly Glu Gly Phe Lys Ala Ser Arg Leu Phe Ala Gly
            485                 490                 495

Ser Ser Glu Arg Ala Thr Phe Val Gln Gln Leu Thr Arg Leu Leu Glu
        500                 505                 510

Arg Asn His Ile Thr Pro Ala Gly Val Leu Leu Ala Gln His Ser Arg
    515                 520                 525

Pro Ser Leu Arg Asp Ile Lys Gly Asn Leu Asn Lys Val Leu Trp
530                 535                 540

Glu Gln Ala Phe Ala Ala Ser Val Trp Gln Ser His Asp Asn Asp Glu
545                 550                 555                 560

Leu Leu Phe Gly Leu Gly Gln Asn Leu Val Lys Asn Gln Ala Leu Ser
            565                 570                 575

Lys Val Leu Gln Gly Gly Tyr Leu Gln Ser Asp Ile Ala Gln Ala Lys
            580                 585                 590

Leu Leu Leu Ala Pro Leu Tyr Glu Gln Trp Arg Ala Gln Ala Ile Glu
            595                 600                 605

Met Glu Thr Gln Arg Val Ala Ser Asn Ala Gly Gln His Pro Gly
    610                 615                 620

Asn Pro Lys Val His Val Phe Asp Gln Val Ala Val Glu Arg Gly Leu
625                 630                 635                 640

Asp Ser Lys Leu Leu Asn Leu Leu Leu Ser Gly Pro Gln Gly Leu Ala
```

```
                    645                 650                 655
Pro Ala Asp Val Ala Leu Arg Pro Thr Val Glu Ala Leu Leu Ser Gly
                660                 665                 670
Asp Gln Gly Arg Ser Leu Arg Lys Gln Ala Leu Phe His Ala Leu Arg
                675                 680                 685
Pro Val Ala Asp Ser Phe Ser Lys Ala Ala Val Pro Val Asn Ala His
                690                 695                 700
Ala Ala Leu Thr Pro Lys Thr Gly Ala Asp Lys Val Met Ile Asn Asn
705                 710                 715                 720
Arg Leu Asn Gln Pro Asp Pro Tyr Leu Ile Leu Asn Thr His Pro Glu
                725                 730                 735
Gln Ala Arg Thr Asp Ala Ala Leu Leu Ile Gln Asp Asp Lys Tyr Arg
                740                 745                 750
Ser Tyr Ser Gln Phe Arg Pro Asp Pro Asn Asn Glu Ala Thr Arg Tyr
                755                 760                 765
Met Ser Asp Leu Asp Thr Pro Phe Val Gly Gly Ile Ser Gly Thr Thr
                770                 775                 780
Gln Thr Val Ser Asn Ala Leu Pro Glu Leu Phe Gly Ser Ala Pro Ser
785                 790                 795                 800
Ile Lys Gln Tyr Trp Gln Phe Gln Met Ala Asn Ala Ala Phe Met Ile
                805                 810                 815
Arg Asn Gly Tyr His Ser Phe Phe Glu Thr Leu Tyr Val Ala Ala Arg
                820                 825                 830
Tyr Glu Pro Gln Gly Pro Asp Ser Ile Gly Lys Asp Leu Leu Gln Thr
                835                 840                 845
Phe Asp Arg Tyr Arg Ala Gln Gly Arg Arg Glu Ala Leu His Gly Glu
850                 855                 860
Leu Tyr Asp Ala Val Met Ala Arg Val Leu Pro Ile Val Asn Gln Gly
865                 870                 875                 880
Leu Ala Pro Ser Glu Glu Phe His Pro Pro Arg Phe Thr Asp Leu Gly
                885                 890                 895
Pro Leu Pro Ala Leu Leu Gly Gln Ala Ala Lys Asp Leu Gln Leu Lys
                900                 905                 910
Thr Gly Leu Ala Ser Leu Gly Ala Gly Phe Glu Pro Arg Gln Gly Ser
                915                 920                 925
Ala Asp Ile His Gln Phe Ala Ala Asp Pro Val Gln Phe Ala Gln Thr
                930                 935                 940
His Thr Leu Ser Ala Glu Ala Leu Val Lys Ala Gly Arg Leu Pro Ala
945                 950                 955                 960
Gln Gly Asn Val Gln Leu Val Glu Val Ala Pro Arg Leu Tyr Glu Leu
                965                 970                 975
Glu Tyr Thr Glu His Ser Ala Asn Ser Val Ser Gly Ser Pro Asp Ser
                980                 985                 990
Val Pro Ala Tyr Phe Leu Gly Tyr Asn Gly Pro Asn Gln Ala Asn Ala
                995                 1000                1005
Ala Pro Ala Tyr Val Asp Ile Pro Lys Gln Ala Arg Pro Gly Ser
                1010                1015                1020
Phe Leu Phe Thr Gly Thr Leu Ser Gly Cys Ser Leu Val Val Thr
                1025                1030                1035
Ser Leu Asp Ala Thr Thr Tyr Arg Val Tyr His Asp Gly Arg Val
                1040                1045                1050
Asn Ser Ser Leu Leu Tyr Asp Asn Val Val Met Ala Val Asp Tyr
                1055                1060                1065
```

```
Lys Asp Tyr Gln Val Ala Gly Thr Ala Glu Gly Leu Ala Ala Ala
    1070                1075                1080

Tyr Met Gln Val Val Asp Gly Gln Trp Gln Leu Val Phe Gln Arg
    1085                1090                1095

Gln Glu Tyr Gln Arg Glu Gly Gln Met Val Trp Pro Lys Leu Arg
    1100                1105                1110

Glu Gly Ala Glu Pro Leu Ala Ile Gln Thr Ala Asp Ser Gln Val
    1115                1120                1125

Gln Glu Arg Asn Arg Thr Gln Phe Ala Glu Tyr Arg Glu Gln Val
    1130                1135                1140

His Gln Asn Leu Lys Lys Val Ala Thr Gln Phe Gly Val Ser Thr
    1145                1150                1155

Glu Gly Val Ala Asp Gly Val Tyr Ser Gly Gly Asp Phe Ser Pro
    1160                1165                1170

Glu His Pro Ala Ile Ala Ala Trp Asn Arg Leu Arg Asp Ala Val
    1175                1180                1185

Gln Ala Lys Val Ser Ala Asp Ile Glu Gln Leu Gly Asn Gln Arg
    1190                1195                1200

Tyr Gln Leu Gln Glu Gln Arg Arg Gly Ala Ser Asp Lys Arg Leu
    1205                1210                1215

Ile Asp Gln Gln Ile Lys Gln Leu Asn Leu Thr Gln Asp Phe Tyr
    1220                1225                1230

Arg Ala Gln Tyr Glu Pro Val Leu Arg Glu Ala Ala Ser Val Glu
    1235                1240                1245

Lys Thr Trp Leu Trp Gln Gln Ile Gln Ala Lys Gln Gly Ser Ala
    1250                1255                1260

Ala Val Val Arg Thr Asp Asp Thr Ala Ile Gln Gly Gly Gly Asp
    1265                1270                1275

Glu Arg Ser Thr Ser Val Gly Glu Arg Tyr Ala Ile Ala Glu Ala
    1280                1285                1290

Tyr Gln Arg Gly Ala Arg Gly Thr Ala Phe Ser Asp Gly Val Arg
    1295                1300                1305

Asp Phe Arg Glu Ile Lys Ile Pro Gly Leu Asp Asp Lys Lys Ser
    1310                1315                1320

Ala Leu Glu Met Lys Arg Leu Phe Leu Asp Gly Gln Leu Thr Pro
    1325                1330                1335

Gly Gln Arg Gly Ala Leu Ser Ala Arg Ile Ser Glu Thr Ser Gln
    1340                1345                1350

Ala Glu Tyr Ile Asp Lys Val Leu Arg Gln Thr Ala Thr Leu Ser
    1355                1360                1365

Glu Asp Phe Arg Gly Ala Gly Ser Val Phe Gly Gln Leu Ala Pro
    1370                1375                1380

Gln Asp Phe Tyr Leu Ser Leu Val Gly Asp Arg Ser Gly Gly Arg
    1385                1390                1395

Cys Tyr Pro Leu Val Arg Ala Met Ala Val Ala Leu Ala Arg Gly
    1400                1405                1410

Gly Glu Ala Gly Val Asn Ser Leu Val Gln Lys Leu Phe Leu Ala
    1415                1420                1425

Ser Ala Asp Pro Gln Ala Gly Ser Ser Thr Leu Leu Lys Asn Ser
    1430                1435                1440

Leu Ile Arg Leu His Ser Asn Val Asp Ala Val Gln Ala Ser Lys
    1445                1450                1455
```

-continued

```
Ala Leu Gly Gln Phe Gln Leu Ser Asp Val Val Ala Arg Leu Ala
1460            1465                1470

Asn Gly Ser Ser Asp Ser Met Phe Ala Leu Asn Thr Gln Asn His
1475            1480                1485

Ser Met Met Val Gly Ser Thr Gln Gly Pro Glu Gly Arg Arg Tyr
1490            1495                1500

Tyr Phe Tyr Asp Pro Asn Val Gly Ile Phe Ala Phe Asp Ser Ser
1505            1510                1515

Lys Gly Leu Ala Lys Ala Met Glu Gln His Leu Val Arg Arg Lys
1520            1525                1530

Leu Ala Ala His Tyr Gly Ser Phe Gly Ser Gln Ser Gln Pro Ala
1535            1540                1545

Phe Asn Leu Val Glu Ile Asp Thr His Lys Met Ala Glu Val Pro
1550            1555                1560

Val Gly Ser Gly Leu Asn Val Ala Asp Leu Ser Arg Pro Glu Glu
1565            1570                1575

Leu Ala Gly Val Ile Gly Gln Arg Arg Gln Val Glu Gln Ala Val
1580            1585                1590

Gly Ala Gln Gln Arg Val Ser Gln Asp Leu Arg Leu Gly Ala Ala
1595            1600                1605

Leu Thr Thr Phe Asp Ala Glu Gln Trp Gly Ala Arg Phe Asp Ala
1610            1615                1620

Ala Ser Thr Arg Leu Ala Arg Glu His Gln Leu Ser Ser Gln Trp
1625            1630                1635

Ile Pro Ile Ile Ala Asn Thr Glu Pro Gln Pro Glu Gly Gly Tyr
1640            1645                1650

Arg Val Gln Phe Ile Asn Arg Asp Gln Pro Asp Gln Thr Arg Trp
1655            1660                1665

Leu Ser Thr Asp Asp Gly Thr Phe Val Glu Phe Arg Arg Phe Val
1670            1675                1680

Asp Glu His Met Ser Val Leu Asn Glu His Phe Thr Leu Glu His
1685            1690                1695

Gly Gln Ile Arg Pro Arg Gly Gly Val Gly Glu Val Ala His Val
1700            1705                1710

Asp Gly Leu Asn Ala Gly Phe Ala Val Gln Thr Leu Ile Gln Trp
1715            1720                1725

Phe Ala Asp Lys Asn Arg Lys Asp Ala Ala Gln Gly Val Val Ser
1730            1735                1740

Pro Asp Leu Ala Thr Ala Leu Lys Ile His Ser Tyr Leu Gly Leu
1745            1750                1755

Ala Gln Ile Gly His Gly Thr Val Gln Asp Val Ala Lys Val Thr
1760            1765                1770

Glu Leu Val Gln Thr Ala Leu Arg Gly Glu Ala Leu Ala Ala Glu
1775            1780                1785

Ser Ser Leu Lys Asp Phe Ala Ser Thr Leu Gly His Thr Val Asn
1790            1795                1800

Glu Gly Ala Gly Val Leu Phe Gly Gly Ala Met Val Gly Leu Asp
1805            1810                1815

Ala Tyr Glu Leu Ala His Ala Glu Asn Asp Val Gln Lys Ala Val
1820            1825                1830

Phe Gly Thr Gln Leu Ala Phe Asp Ser Ala Ser Phe Val Ser Gly
1835            1840                1845

Ala Ala Gly Ile Gly Ala Gly Leu Ile Gly Ala Ser Thr Thr Ala
```

-continued

```
            1850                1855                1860
Ala Val Leu Gly Gly Ala Gly Val Ile Leu Gly Gly Leu Ala Val
            1865                1870                1875
Gly Phe Thr Ala Leu Ala Gln Ala Phe Gly Ala Val Ala Glu Asp
            1880                1885                1890
Ala Lys Ala Val Gly Arg Tyr Phe Asp Thr Leu Asp Lys Ala Tyr
            1895                1900                1905
Gln Gly Asn Gly Tyr Arg Tyr Asp Glu Lys Gln Gln Val Leu Val
            1910                1915                1920
Pro Leu Ala Gly Ala Val Val Lys Arg Leu Asp Leu Arg Ser Asn
            1925                1930                1935
Glu Val Gly Phe Asp Ser Gln Tyr Ile Tyr Arg Thr His His Gly
            1940                1945                1950
Ser Thr Gly Ser Gly Ala Ile Asn Tyr Phe Phe Trp Val Gly Asp
            1955                1960                1965
Phe Pro Arg Met Ile His Asp Arg Ala Gln Ala Ile Glu Val Arg
            1970                1975                1980
Ser Gly Ile Gly His Gly Ala Lys Pro Pro Arg Leu Asp His Gly
            1985                1990                1995
Asp Ser Arg Thr Val Ile Leu Pro Gly Thr Pro Lys Ser Tyr Ile
            2000                2005                2010
Ser Tyr Glu Tyr Met Ile Leu Pro Gly Ala Thr Thr Arg His Asp
            2015                2020                2025
Thr Gly Phe Asp Val Ile Arg Lys Leu Glu Gln Asp Arg Arg Phe
            2030                2035                2040
Asp Tyr Asp Phe Tyr Ile Phe Pro Ser Glu Glu Thr Ile Arg Arg
            2045                2050                2055
Ile His Gln Glu Tyr Val Glu Thr Pro Val Glu Val Leu Leu Asp
            2060                2065                2070
Gly His Asn Arg Gln Leu Val Val Pro Gln Leu Pro Lys Glu Leu
            2075                2080                2085
Tyr Gly Tyr Leu Arg Tyr Asp Ile Gln Gly Ala Gly Gly Glu Tyr
            2090                2095                2100
Leu Ile Gly Leu Asn Glu Gly Thr Glu Val Arg Leu Ser Asn Glu
            2105                2110                2115
Ala Gly Arg Gln Pro Ser Arg Trp Ile Ile Asp Ser Ser Gln Leu
            2120                2125                2130
Glu Ser Asp Ser Ile Thr Val Ala Lys Asp His Leu Leu Val Gly
            2135                2140                2145
Gly Val Lys Val Arg Leu Asp Pro Ala Gln Ser Gly Gln Val Leu
            2150                2155                2160
Leu Val Asn Ala Lys Gly Glu Val Arg Ala Ala Asp Phe Ala Gly
            2165                2170                2175
Gln Thr Thr Tyr Val Val Lys Glu Asp Ala Ser Gln Trp Gln Val
            2180                2185                2190
Ser Gly Gln Arg Ile Glu Gln His Leu Lys Glu Leu Ala Gln Ala
            2195                2200                2205
His Gln Leu His Gly Gln Tyr Val Val Val Glu Asn Tyr Lys His
            2210                2215                2220
Gly Glu Arg Asn Val Gly Arg Ala Tyr Tyr Glu Val Ala Lys Asp
            2225                2230                2235
Arg Met Leu Phe Thr Asp Thr Asp Val Gln Gln Ala Arg Asn Ala
            2240                2245                2250
```

```
Gln Leu Gly Ala Val Ile Gly Glu His Ala Tyr Phe Val Asp Ala
    2255                2260                2265

Glu Asn Ala Ala Ala Trp Arg Val Asp Ile Ala Ser Gly Lys Val
    2270                2275                2280

Asp Ala Gln Phe Ala Pro Ala Phe Asn Gln Ser Ala Gly Gln Ile
    2285                2290                2295

Ser Arg Phe Trp Gln Glu Gly Asp Ala Val Tyr Leu Ala Arg Arg
    2300                2305                2310

Tyr Gln Leu Lys Glu Arg Glu Ala Glu Leu Ser Phe Arg Ile Leu
    2315                2320                2325

Gly Asp Arg Met Glu Leu Val Gly Val Val Gly Asp Glu Ser Leu
    2330                2335                2340

Leu Gln Leu Ser Ala Ser Asn Ser Gln His Gly Lys Asp Ala Lys
    2345                2350                2355

Thr Leu Leu Asn Thr Leu Leu Lys Gly Tyr Glu Thr Gln Ala Thr
    2360                2365                2370

Gln Arg Asp Thr Pro Val Tyr Ser Leu Gly Ala Pro Val Leu Glu
    2375                2380                2385

Pro Thr Ala Ala Glu Leu Ile Thr Val Phe Gly Leu Asp Asn Ala
    2390                2395                2400

Lys Val Ala His Arg Tyr Trp Val Arg Ser Ser Asp Gly Ile Val
    2405                2410                2415

Ile Lys Pro Asn Leu Ala Pro Pro Ala Gly Gln Ala Pro Arg Ala
    2420                2425                2430

Asp Ala Pro Gly Gln Ala Gln Ser Ala Trp Gln Ile Pro Ala Asp
    2435                2440                2445

Leu Val Leu Ala Gly Ser Gln Ala Gln Pro Gly Gly Gln Glu Val
    2450                2455                2460

Phe Tyr Phe Tyr Ser Lys Ala Gln Gln Val Leu Phe Arg Gln Glu
    2465                2470                2475

Gly Pro Gly Gln Lys Val Leu Asp Ala Gly Gln Pro Ser Ala Leu
    2480                2485                2490

Arg Leu Ser Thr Pro Pro Leu Ala Asn Val Leu Asn Leu Asn Gly
    2495                2500                2505

His Leu Leu Ala Val Thr Asn Asp Gly Arg Met Ala Arg Ile Glu
    2510                2515                2520

Ala Thr Gly Arg Leu Ser Tyr Glu Ala Val Asn Glu His Trp Leu
    2525                2530                2535

Lys Ala His Ser Asn Trp Trp Lys Asn Leu Ala Glu Val Ala Gly
    2540                2545                2550

Ser Asn Ala Thr Leu Ala Val Phe Gly Val Lys Ala Ala Asp Gly
    2555                2560                2565

Lys Ser Ala Leu Pro Val Trp Tyr His Asn Gly Gln Val Val Val
    2570                2575                2580

Ala Ser Ser Ala Leu Gln Gly Lys Pro Leu Gln Phe Leu Gly Phe
    2585                2590                2595

Asp Ser Ala Ser Ala Ser Ala Arg Leu Phe Glu Pro Glu Ser Gly
    2600                2605                2610

Lys Leu Tyr Leu Gln Pro Pro Leu Thr Ala Gln Ala Leu Ala Thr
    2615                2620                2625

Ala Phe Gly Lys Asp Glu Val Leu Glu Ala Ser Ala Gln Leu Pro
    2630                2635                2640
```

```
Ala Ala Ile Asp Trp Met Pro Lys Gln Pro Leu Arg Ser Ala Val
2645                2650                2655

Gln Val Asp Ala Gly Leu Arg Leu Thr Thr Val Gln Gly Glu Val
2660                2665                2670

Leu Leu Arg Ser Asn Asn Gly Asp Val Gln Leu Val Ala Val Asp
2675                2680                2685

Lys Gly Trp Gln Gln Ala His Leu Gly Asn Leu Pro Gln Ala Leu
2690                2695                2700

Ala Thr Val Ala Gly Gln Trp Gly Ala Lys Gly Val Leu Ser Leu
2705                2710                2715

Gln Asp Gly Asp Thr Arg Gly Trp Phe Asp Ile Ala Ser Gly Gln
2720                2725                2730

Met Phe Ala Ser Asn Gly Ile Pro Gly Gly Ser Asp Leu Arg Phe
2735                2740                2745

Ile Gly Val Ala Ala Gly Thr Pro Asn Ser Ala Tyr Val Tyr Ser
2750                2755                2760

Pro Thr Ala Gln Ala Leu Tyr Gln Val Lys Asp Gly Lys Ala Leu
2765                2770                2775

Gln Leu Gly His Tyr Ala Asn Val Glu Arg Ile Gly Ser Ser Leu
2780                2785                2790

Leu Leu Gln Gly Ala Ser Gly Asn Ala Pro Gln Asp Asp Leu Ala
2795                2800                2805

Pro Pro Leu Ile Ala Gly Val Asp Ser Val Val Leu His Gly Gly
2810                2815                2820

Ala Gly Asp Asp Thr Tyr Arg Phe Ser Pro Ala Met Trp Ala His
2825                2830                2835

Tyr Arg Ser Val Val Ile Asp Asn Asp Pro Gly Leu Ala Leu
2840                2845                2850

Asp Arg Val Ile Leu Pro Val Ala Asp Gly Lys Asn Ile Leu Val
2855                2860                2865

Ser Arg Arg Gly Glu Asp Val Gln Leu Thr Asp Thr Gly Asn Gly
2870                2875                2880

Thr Ala Leu Val Leu Arg Gln Val Leu Gly Ser Gln Ala Ala Ala
2885                2890                2895

His Gly His Leu Leu Ile Glu Leu Lys Gly Asp Ser Ser Met Ile
2900                2905                2910

Ser Val Glu Gln Leu Leu Lys Gly Phe Gly Pro Ser Gly Ser Ala
2915                2920                2925

Gly Asp Ser Val Phe Glu Leu Ala Trp Ser Gln Arg Glu Thr Leu
2930                2935                2940

Pro Ala Ala Asn Ala Leu Ser Ser Ala Ala Asp Val Pro Asp Ser
2945                2950                2955

Ala Ala Asp Gly Arg Gly Pro Ser Leu Ala Lys Leu Ser Gly Ala
2960                2965                2970

Met Ala Ala Phe Ala Asp Thr Gly Gly Ala Arg Glu Gln Leu Pro
2975                2980                2985

Lys Asn His Gln Ala Ala Gln Ala Val Leu Val Pro Ser Leu Thr
2990                2995                3000
```

USE OF PROTEINS TO CONTROL MOLLUSCS

CROSS-REFERENCE TO RELATED APPLICATIONS

This application claims priority to, and is the National Stage of International Application No. PCT/US2016/033945 filed on May 24, 2016 and claims the priority of U.S. Provisional Patent Application Ser. No. 62/167,860, filed on May 28, 2015, the contents of which are incorporated by reference herein in their entirety.

TECHNICAL FIELD OF THE INVENTION

The present disclosure relates in general to the field of proteins having molluscicidal activity.

STATEMENT OF FEDERALLY FUNDED RESEARCH

None.

INCORPORATION-BY-REFERENCE OF MATERIALS FILED ON COMPACT DISC

None.

BACKGROUND ART

Without limiting the scope of the invention, its background is described in connection with proteins having molluscicidal. The ability of the mussels to quickly colonize new areas, rapidly achieve high densities and attach to any hard substratum (e.g., rocks, logs, aquatic plants, shells of native mussels, exoskeletons of crayfish, plastic, concrete, wood, fiberglass, pipes made of iron and polyvinyl chloride and surfaces covered with conventional paints) make it possible for them to cause serious adverse consequences. These consequences include damages of water-dependent infrastructure, millions of dollars increase in the operating expense and significant damage to the ecological systems.

Management of mussels is very important for protecting water-dependent infrastructure and aquatic ecological systems. There are many proactive and reactive methods to control and reduce the populations of mussels. Reactive removal includes the mechanical removal, predator removal, and chemical and biochemical removal of adult mussels. For example, fish, birds, crayfish, crabs, leeches and mammals have shown to predate mussels. However, it is unlikely that invasive mussel populations will be controlled by natural predation, especially in man-made structures such as pipes or pumping plants. Proactive measures to control mussels includes any mechanical, physical or chemical means in which the planktonic (veliger) mussel life stage is prevented from settling and growing into the adult life stage or colonizing on hard substrates. Preventing mussels from colonizing and growing into adult life stages is also referred to as settlement prevention

DISCLOSURE OF THE INVENTION

The present invention includes a method for controlling molluscs in a liquid location comprising administering an effective amount of a composition having protein that is 80% identical to SEQ ID NO: 1, to control said mollusk at said liquid location. The liquid location can be a body of water or paint, or in pipes filled with liquid.

In one aspect the protein has 90%, 95%, 98%, 99%, or 100% sequence identity to SEQ ID NO:1.

In another aspect the protein has 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% sequence identity to SEQ ID NO: 1.

In another aspect, the present disclosure denotes the composition that can further comprise gamma-dodecalactone, delta-tridecalactone, piliferolide A, alpha-heptyl-gamma-butyrolactone or 11-hydroxy-12-ene-octadecanoic acid.

Yet in another aspect, the said composition further comprises an inert material.

DESCRIPTION OF THE DRAWINGS

For a more complete understanding of the features and advantages of the present invention, reference is now made to the detailed description of the invention along with the accompanying figures and in which.

DESCRIPTION OF THE INVENTION

Figure 1:
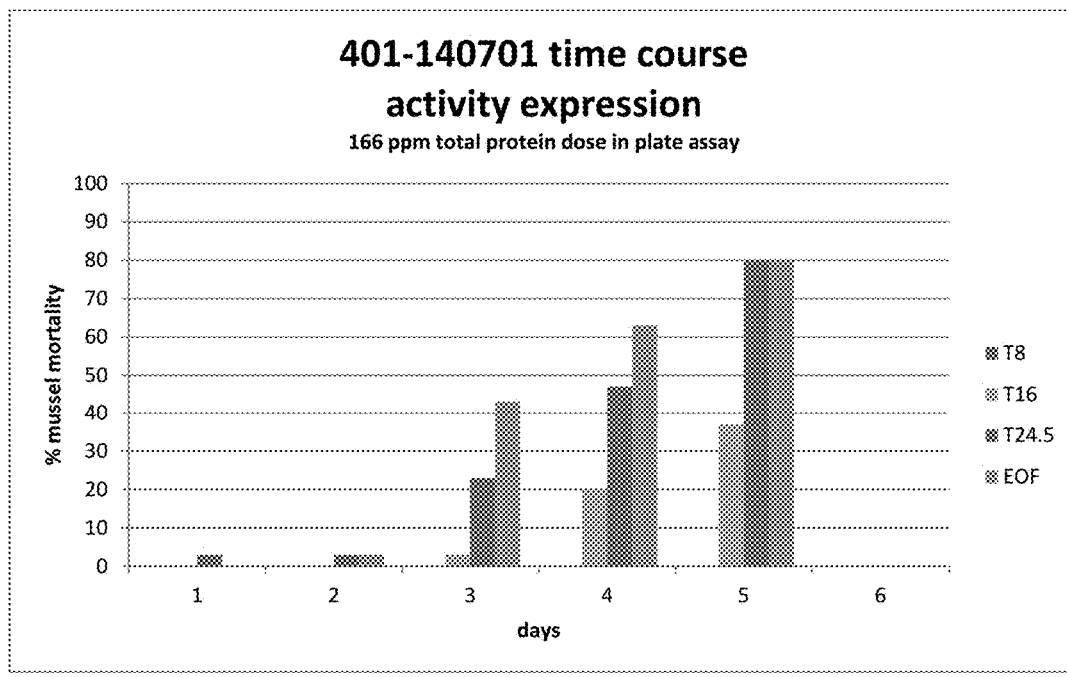
FIG. 1 denotes a plot of the mussel mortality of the cell lysates vs. the days of the mussel assay.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As defined herein, "whole broth culture" or "whole cell broth" refers to a liquid culture containing both cells and media. If bacteria are grown on a plate, the cells can be harvested in water or other liquid, whole culture. The terms "whole broth culture" and "whole cell broth" are used interchangeably.

As defined herein, "supernatant" refers to the liquid remaining when cells grown in broth or are harvested in another liquid from an agar plate and are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer, organic solvent) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal and particularly, molluscicidal activity.

As defined herein, "carrier" is an inert, organic or inorganic material, with which the active ingredient is mixed or formulated to facilitate its application to plant or other object to be treated, or its storage, transport and/or handling.

As defined herein, "controlling molluscs" means controlling the eggs, larvae, veligers and post-veligers of the molluscs by killing or disabling them so that they cannot colonize, grow, establish, or reproduce in a given location.

As defined herein, "derived from" and "obtainable from" means directly isolated or obtained from a particular source or alternatively having identifying characteristics of a substance or organism isolated or obtained from a particular source. These terms are used interchangeably throughout the specification.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods. The skilled artisan will recognize that the percentages may be of any incremental value between 20-100%, and each and every value covered in that range need not be specifically listed herein.

As defined herein, a "nucleic acid molecule", is intended to include DNA molecules and RNA molecules. A nucleic acid molecule may be single-stranded or double-stranded, but preferably is double-stranded DNA.

As defined herein, a "vector", is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As defined herein, the terms "recombinant host cell" and "transformed host cell" are used interchangeably and refer to a cell into which a recombinant expression vector and/or an isolated nucleic acid molecule has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet et al., Nucleic Acids Research 16:10881-90 (1988); Huang et al., Computer Applications in the Biosciences 8:155-65 (1992), and Pearson et al., Methods in Molecular Biology 24:307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See Current Protocols in Molecular Biology, Chapter 19, Ausubel et al., Eds., Greene Publishing and Wiley-Interscience, New York (1995); Altschul et al., J. Mol. Biol., 215:403-410 (1990); and, Altschul et al., Nucleic Acids Res. 25:3389-3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see e.g., Karlin & Altschul, Proc. Nat'l. Acad. Sci. USA 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Clayerie and States, Comput. Chem., 17:191-201 (1993)) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (J. Mol. Biol. 48:443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89:10915).

Multiple alignment of the sequences can be performed using the CLUSTAL method of alignment (Higgins and Sharp (1989) CABIOS. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An effective amount is defined as that quantity of proteins, microorganism cells, supernatant, whole cell broth, filtrate, cell fraction or extract, metabolite and/or compound alone or in combination with another pesticidal substance that is sufficient to control molluscs. The effective rate can be affected by pest species present, stage of pest growth, pest population density, and environmental factors such as temperature, rain, time of day and seasonality. The amount that will be within an effective range in a particular instance can be determined by laboratory or field tests.

In one embodiment, the protein used in the methods for controlling molluscs has about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% homology or sequence identity to SEQ ID NO: 1.

Also provided are nucleic acid molecules that encode said protein SEQ ID NO: 1. These nucleic acid molecules may be DNA, RNA, cDNA, cRNA or analog sequences. They can be obtained from a *Pseudomonas* strain or by chemical synthesis or by recombinant methods known in the art. Specifically nucleic acid libraries may be constructed, screened and amplified. For example, a cDNA or genomic library can be screened using a probe based upon the sequence of a polynucleotide disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

These nucleic acid molecules can be inserted into vectors. The vectors may be expression vectors. Recombinant expression vectors containing a sequence encoding these nucleic acid molecules are thus provided. The expression vector can contain one or more additional polynucleotide sequences, such as but not limited to regulatory sequences, a selection marker, a purification tag, or a polyadenylation signal. Such regulatory elements can include a transcriptional promoter, enhancers, mRNA ribosomal binding sites, or sequences that control the termination of transcription and translation.

Expression vectors, especially mammalian expression vectors, can include one or more non-transcribed elements, such as an origin of replication, a suitable promoter and enhancer linked to the gene to be expressed, other 5' or 3' flanking non-transcribed sequences, 5' or 3' non-translated sequences (such as necessary ribosome binding sites), a polyadenylation site, splice donor and acceptor sites, recombination sites, or transcriptional termination sequences. An origin of replication that confers the ability to replicate in a specific host may also be incorporated.

The vectors may be used to transform any of a wide array of host cells known to those of skill in the art. Vectors include without limitation, plasmids, phagemids, cosmids, bacmids, bacterial artificial chromosomes (BACs), yeast artificial chromosomes (YACs), and baculovirus vectors, as well as other bacterial, eukaryotic, yeast, and viral vectors The proteins can be obtained, or are obtainable or derived from an organism having the identifying characteristics of a *Pseudomonas* species, more particularly, from an organism having the identifying characteristics of a strain of *Pseudomonas fluorescens* or alternatively from an organism having the identifying characteristics of *Pseudomonas fluorescens* isolate, ATCC 55799 as set forth in U.S. Pat. No. 6,194,194. The methods comprise cultivating these organisms and optionally obtaining the proteins by isolating these proteins from the cells of these organisms.

In particular, the organisms are cultivated in nutrient medium using methods known in the art. The organisms can be cultivated by shake flask cultivation, small scale or large scale fermentation (including but not limited to continuous, batch, fed-batch, or solid state fermentations) in laboratory or industrial fermenters performed in suitable medium and under conditions allowing cell growth. The cultivation can take place in suitable nutrient medium comprising carbon and nitrogen sources and inorganic salts, using procedures known in the art. Suitable media may be available from commercial sources or prepared according to published compositions.

After cultivation, a substantially pure culture or whole cell broth comprising said strain, or cell fraction, supernatant, filtrate, compound (e.g., metabolite) and/or extract of or derived from said *Pseudomonas protegens* can be used in formulating a composition of the present disclosure. Alternatively, after cultivation, the proteins and/or metabolites can be extracted from the culture broth. Alternatively, after cultivation, the cells in the pure culture or whole cell broth may be lysed. The lysed cultivation may be unpurified or purified and used in a formulation for controlling molluscs in a liquid. The purification may vary in degree from removal of cellular debris and/or nucleic acids, to the isolation of specific classes of compounds or individual compounds that are used in a formulation for controlling molluscs in a liquid. In one embodiment, after cultivation, the proteins and/or metabolites are extracted from the culture broth and are used in a formulation for controlling molluscs. Alternatively, after cultivation, a substantially pure cell fraction, supernatant, filtrate, and/or extract of or derived from said strain can be used in formulating a composition for controlling molluscs in a liquid location. Alternatively, after cultivation, one or more proteins and/or metabolites can be extracted and used in formulating a composition for controlling molluscs in a liquid location. The extract can be fractionated by chromatography. Chromatographic fractions can be assayed for toxic activity against, for example, molluscs. This process may be repeated one or more times using the same or different chromatographic methods.

The proteins set forth above can be formulated in any manner. Non-limiting formulation examples include, but are not limited to, emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), etc. In any formulation described herein, percent of the active ingredient is within a range of about 0.01% to 99.99% including each incremental variation in the range even though they are not explicitly listed.

The compositions can be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower. A composition can comprise gel-encapsulated active ingredient(s). Such gel-encapsulated materials can be prepared by mixing a gel-forming agent (e.g., gelatin, cellulose, or lignin) with a culture or suspension of live or inactivated *Pseudomonas protegens*, or a cell-free filtrate or cell fraction of a *Pseudomonas protegens* culture or suspension, or a spray- or freeze-dried culture, cell, or cell fraction or in a solution of pesticidal compounds used in the method of the invention; and inducing gel formation of the agent.

The composition can additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) sorbitan monolaurate. The concentration of surfactants may range between about 0.1-35% (including each incremental variation in the range even though they are not explicitly listed) of the total formulation; a preferred range is about 5-25% (including each incremental variation in the range even though they are not explicitly listed)). The choice of dispersing and emulsifying agents, such as non-ionic, anionic, amphoteric and cationic dispersing and emulsifying agents, and the amount employed is determined by the nature of the composition and the ability of the agent to facilitate the dispersion of the proteins of the present disclosure.

In another embodiment, the proteins set forth herein can be used in controlling molluscs, particularly members of the Gastropoda and/or Bivalvia classes and more particularly mussels, snails and slugs.

Methods of Use. The proteins of the present disclosure (SEQ ID No. 1) can be used to control molluscs, particularly, a member of the Gastropoda and/or Bivalvia class, more particularly mussels (e.g., *Dreissana* species) and/or Gastropoda, particularly, snails, which includes but is not limited to aquatic snails (e.g., *Biomphalaria* species) and garden snails, including but not limited to brown garden snails, white garden snails (e.g., *Cantareus* species, *Cornu* species, *Theba* species), and/or slugs, including but not limited to gray garden slug (e.g., *Deroceras* sp.), the banded or threeband slug (e.g., *Lehmannia* sp.), the tawny slug (e.g., *Limacus* sp.), and the greenhouse slug (e.g., *Milax* sp.) in a body of water or on surfaces where molluscs such as mussels, snails and/or slugs gather or alternatively as an anti-fouling agent in paint. In the event that it is used as an antifouling agent in paint, it is present in an anti-vegetative, biocidally effective amount. Surfaces used by molluscs (such as mussels, snails and/or slugs) include but are not limited to plastic, concrete, wood, fiberglass, pipes made of iron and polyvinyl chloride and surfaces covered with paints and/or coatings. Coatings may be formulated from pigments, binders, additives, and/or carrier fluids and are preferably applied in a thin film to provide protection or decoration to a surface. The end product (which contains the active compound) will be used at 10-200 mg/L, more specifically at 25-100 mg/L (ppm) or 25-10000 mg/kg (including each incremental variation in the range even though they are not explicitly listed). It will be applied either as a dry product or suspended in water into pipes, dam structures, holding tanks, and open waters such as streams, lakes, irrigation canals, ponds and lakes through specific application pumps and mixing systems.

Yet in another embodiment, the present disclosure depicts a composition including other metabolites that have molluscicidal activity. For example, lactones and fatty acids as disclosed in U.S. Pat. No. 8,968,723.

The present disclosure is also directed to a method comprising a step of administering a composition having a protein (e.g., SEQ ID NO: 1), and in combination of an inert material such as clay to enhance the uptake and hence, mortality of mussels.

Examples of the inert material that may be used in the compositions of the present disclosure include, but are not limited to, inorganic minerals such as kaolin, mica, gypsum, phyllosilicates, carbonates, sulfates, or phosphates; or botanical materials such as wood products, cork, powdered corn cobs, rice hulls, peanut hulls and walnut shells. In a particular embodiment, the inert material can be obtained or derived from a clay mineral (kaolinite, smectite, attapulgite) suspended in water at a rate of about 1 to 20 mg/liter corresponding to approximately 1 to 20 NTU (normalized turbidity units). The inert materials used to enhance mussel siphoning can be applied in solid form or as a suspension in aqueous solution, preferably water, directly to the water or the location (e.g., solid surface) where the mussels are treated. In a particular embodiment, to enhance product efficacy, an inert material such as clay, silt, sediment or any other material with no nutritional value and with a small enough particle size can be suspended in water prior to the treatment with a chemical or a biopesticide product.

Conservative Substitutions and Functional Fragments. In comparing amino acid sequences, residue positions which are not identical can differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. With respect to a reference polypeptide sequence, a test polypeptide sequence that differs only by conservative substitutions is denoted a "conservatively substituted variant" of the reference sequence.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are known in the art. Similarly, methods for determining protein function are known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, either genetic and biochemical. See, for example, Fields et al. (1989) Nature 340:245 246; U.S. Pat. No. 5,585,245 and PCT WO 98/44350.

Typically, a functional fragment retains at least 50% of the activity or function of the polypeptide. In some embodiments, a functional fragment retains at least 60%, at least 70%, at least 80%, at least 90%, at least 95%, at least 99% or 100% (including each incremental variation in the range even though they are not explicitly listed) of the activity or function of the polypeptide.

A functional fragment of a polypeptide can include conservative amino acid substitutions (with respect to the native polypeptide sequence) that do not substantially alter the activity or function of the polypeptide. The term "conservative amino acid substitution" refers to grouping of amino acids on the basis of certain common structures and/or properties. With respect to common structures, amino acids can be grouped into those with non-polar side chains (glycine, alanine, valine, leucine, isoleucine, methionine, proline, phenylalanine and tryptophan), those with uncharged polar side chains (serine, threonine, asparagine, glutamine, tyrosine and cysteine) and those with charged polar side chains (lysine, arginine, aspartic acid, glutamic acid and histidine). A group of amino acids containing aromatic side chains includes phenylalanine, tryptophan and tyrosine. Heterocyclic side chains are present in proline, tryptophan and histidine. Within the group of amino acids containing non-polar side chains, those with short hydrocarbon side chains (glycine, alanine, valine. leucine, isoleucine) can be distinguished from those with longer, non-hydrocarbon side chains (methionine, proline, phenylalanine, tryptophan). Within the group of amino acids with charged polar side chains, the acidic amino acids (aspartic acid, glutamic acid) can be distinguished from those with basic side chains (lysine, arginine and histidine).

A functional method for defining common properties of individual amino acids is to analyze the normalized frequencies of amino acid changes between corresponding proteins of homologous organisms (Schulz, G. E. and R. H. Schirmer, Principles of Protein Structure, Springer-Verlag, 1979). According to such analyses, groups of amino acids can be defined in which amino acids within a group are preferentially substituted for one another in homologous proteins, and therefore have similar impact on overall protein structure (Schulz, G. E. and R. H. Schirmer, supra). According to this type of analysis, conservative amino acid substitution" refers to a substitution of one amino acid residue for another sharing chemical and physical properties of the amino acid side chain (e.g., charge, size, hydrophobicity/hydrophilicity). Following are examples of amino acid residues sharing certain chemical and/or physical properties:

(i) amino acids containing a charged group, consisting of Glu, Asp, Lys, Arg and His, (ii) amino acids containing a positively-charged group, consisting of Lys, Arg and His, (iii) amino acids containing a negatively-charged group, consisting of Glu and Asp, (iv) amino acids containing an aromatic group, consisting of Phe, Tyr and Trp, (v) amino acids containing a nitrogen ring group, consisting of His and Trp, (vi) amino acids containing a large aliphatic non-polar group, consisting of Val, Leu and Ile, (vii) amino acids containing a slightly-polar group, consisting of Met and Cys, (viii) amino acids containing a small-residue group, consisting of Ser, Thr, Asp, Asn, Gly, Ala, Glu, Gln and Pro, (ix) amino acids containing an aliphatic group consisting of Val, Leu, Ile, Met and Cys, and (x) amino acids containing a hydroxyl group consisting of Ser and Thr.

Certain "conservative substitutions" may include substitution within the following groups of amino acid residues: gly, ala; val, ile, leu; asp, glu; asn, gln; ser, thr; lys, arg; and phe, tyr.

Thus, as exemplified above, conservative substitutions of amino acids are known to those of skill in this art and can be made generally without altering the biological activity or function of the resulting molecule. Those of skill in this art also recognize that, in general, single amino acid substitutions in non-essential regions of a polypeptide do not substantially alter biological activity. See, e.g., Watson, et al., "Molecular Biology of the Gene," 4th Edition, 1987, The Benjamin/Cummings Pub. Co., Menlo Park, Calif., p. 224.

Polypeptides of the present disclosure encompass those having 1, 2, 3, 4, 5, 6, 7, 8, 9 or 10 or more amino acid substitutions compared to an amino acid sequence as set forth in SEQ ID NO: 1, e.g., conservative amino acid substitutions. Amino acid residues that can be substituted can be located at residue positions that are not highly conserved. The ordinarily skilled artisan will appreciate that, based on location of the active sites and/or on homology to related proteins, a protein will tolerate substitutions, deletions, and/or insertions at certain of its amino acid residues, without significant change in its overall physical and chemical properties.

Polypeptides of the present disclosure encompass those having an amino acid sequence that is at least 75%, at least 80%, at least 90%, at least 95%, at least 96%, at least 97%, at least 98%, at least 99%, at least 99.5%, at least 99.8% or 100% identical to any of the polypeptides shown in SEQ ID NO: 1.

EXAMPLES

Sample aliquots of whole cell broth were removed from a 100 L fermentation of *Pseudomonas protegens* CL145A at 8, 16, 24.5 and 33 hours (EOF, end of fermentation). The supernatant free whole cell paste was lysed by sonication, and the lysates were examined for activity by live mussel bioassay and analyzed by SDS-PAGE. FIG. 1 is a plot of the mussel mortality of the cell lysates vs. the days of the mussel assay.

Figure 2:
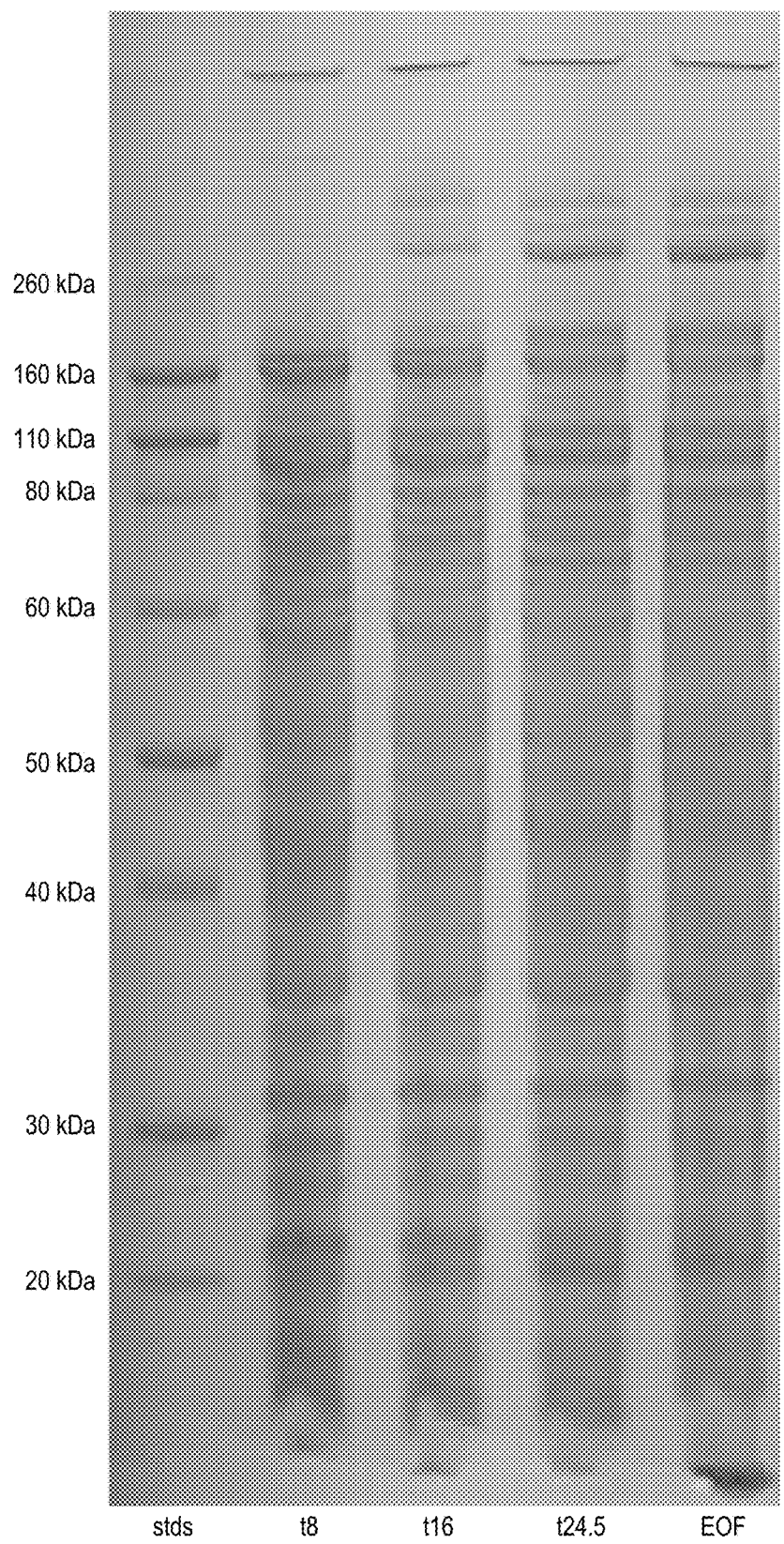
FIG. 2 denotes at least three HMW proteins >260 kDa where expression correlates to the mussel mortality in FIG. 1.

Mussel activity of the cell lysates is very low over the first 16 hours of the fermentation and reaches the highest level at the end of the fermentation. SDS-PAGE (FIG. 2) clearly reveals at least three HMW proteins >260 kDa where expression correlates to the mussel mortality in FIG. 1.

Figure 3:
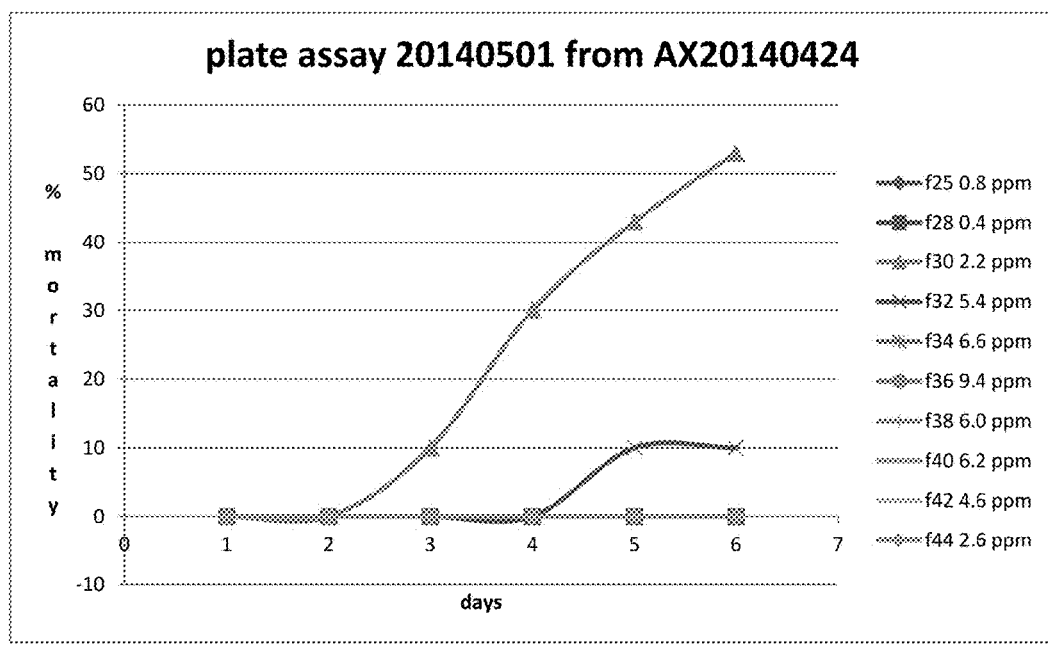
FIG. 3 is a plot of the fraction activity.
Figure 4:
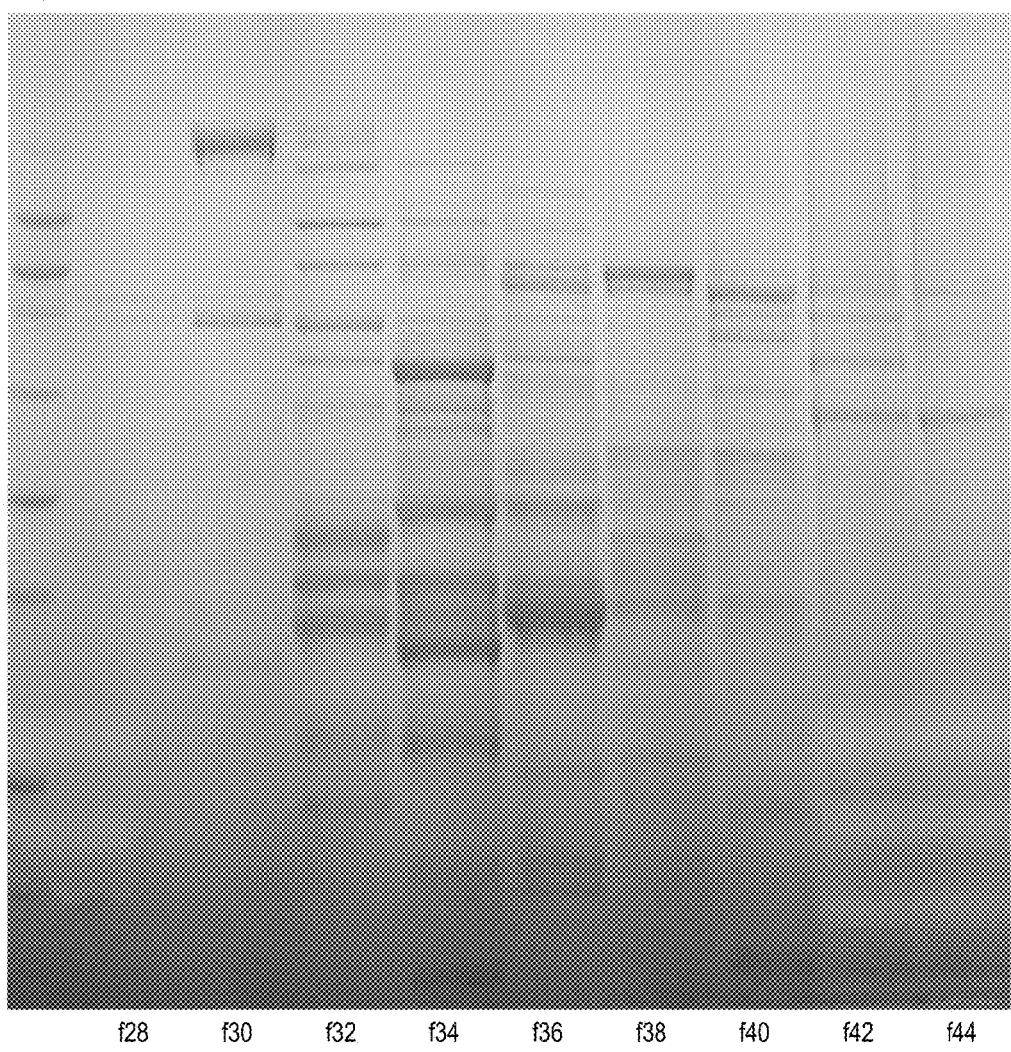
FIG. 4 is the SDS-PAGE of the fractions.

The supernatant (SN) from *P. protegens* EOF cell lysate was fractionated via Q-sepharose anion exchange chromatography and the fractions were bioassayed for mussel killing activity. FIG. 3 is a plot of the fraction activity and FIG. 4 is the SDS-PAGE of the fractions.

The HMW band was excised from an SDS-PAGE gel and submitted to UC Davis proteomics for protein identification via peptide matching. The resultant protein has the following sequence:

(SEQ ID No. 1)
MAFMSKDFTRLLNTLIDQQIKTAGRQTEWFNMSADERAAYIGQVGERLLE
MQQSTLSVLAAQHYQMQDNPVSVGDQLQVLQQRRKEMKAIADTPATIAYK
QQLDRDILLYSRQDTAISHYDSTWNKALRLLSPGGAKAEVLQADAPAKQK
ELKGRINRLEKHLSLQVADSTFSQTYVTLFSELQAYKEVSTRYNAWLKAA
PQQQAASLDALAKPPRASDELPVNLSLLMMEERPGYIRMNVALVNASTDG
RFKDFYLEHGRLVVPTDGVLNFSFGTAARSLAWQQQYRLKSEPPSMRSPT
YAPIRSVLVKTGFVEQYFANHLVSESSLREGFKAQVLSNGRKLLLTGVDR
KVPNQVGIQVSGQSPGTSVTREVPLAGALSELINQNADITSFQTLGVEDY
RQNSYHPDRDGLFVNIHELERSVGFAEHQYLLEMPQGDAYRSATPFAVMT
VEGDKVSSSHLSKAQTETLYQYNAAFFERLEQLRGEGFKASRLFAGSSER
ATFVQQLTRLLERNHITPAGVLLAQHSRPSLRDIKGNNLNKVLWEQAFAA
SVWQSHDNDELLFGLGQNLVKNQALSKVLQGGYLQSDIAQAKLLLAPLYE
QWRAQAIEMETQRVASANAGQHPGNPKVHVFDQVAVERGLDSKLLNLLLS
GPQGLAPADVALRPTVEALLSGDQGRSLRKQALFHALRPVADSFSKAAVP
VNAHAALTPKTGADKVMINNRLNQPDPYLILNTHPEQARTDAALLIQDDK
YRSYSQFRPDPNNEATRYMSDLDTPFVGGISGTTQTVSNALPELFGSAPS
IKQYWQFQMANAAFMIRNGYHSFFETLYVAARYEPQGPDSIGKDLLQTFD
RYRAQGRREALHGELYDAVMARVLPIVNQGLAPSEEFHPPRFTDLGPLPA
LLGQAAKDLQLKTGLASLGAGFEPRQGSADIHQFAADPVQFAQTHTLSAE
ALVKAGRLPAQGNVQLVEVAPRLYELEYTEHSANSVSGSPDSVPAYFLGY
NGPNQANAAPAYVDIPKQARPGSFLFTGTLSGCSLVVTSLDATTYRVYHD
GRVNSSLLYDNVVMAVDYKDYQVAGTAEGLAAAYMQVVDGQWQLVFQRQE
YQREGQMVWPKLREGAEPLAIQTADSQVQERNRTQFAEYREQVHQNLKKV
ATQFGVSTEGVADGVYSGGDFSPEHPAIAAWNRLRDAVQAKVSADIEQLG
NQRYQLQEQRRGASDKRLIDQQIKQLNLTQDFYRAQYEPVLREAASVEKT
WLWQQIQAKQGSAAVVRTDDTAIQGGGDERSTSVGERYAIAEAYQRGARG
TAFSDGVRDFREIKIPGLDDKKSALEMKRLFLDGQLTPGQRGALSARISE
TSQAEYIDKVLRQTATLSEDFRGAGSVFGQLAPQDFYLSLVGDRSGGRCY
PLVRAMAVALARGGEAGVNSLVQKLFLASADPQAGSSTLLKNSLIRLHSN
VDAVQASKALGQFQLSDVVARLANGSSDSMFALNTQNHSMMVGSTQGPEG
RRYYFYDPNVGIFAFDSSKGLAKAMEQHLVRRKLAAHYGSFGSQSQPAFN
LVEIDTHKMAEVPVGSGLNVADLSRPEELAGVIGQRRQVEQAVGAQQRVS
QDLRLGAALTTFDAEQWGARFDAASTRLAREHQLSSQWIPIIANTEPQPE
GGYRVQFINRDQPDQTRWLSTDDGTFVEFRRFVDEHMSVLNEHFTLEHGQ
IRPRGGVGEVAHVDGLNAGFAVQTLIQWFADKNRKDAAQGVVSPDLATAL
KIHSYLGLAQIGHGTVQDVAKVTELVQTALRGEALAAESSLKDFASTLGH
TVNEGAGVLFGGAMVGLDAYELAHAENDVQKAVFGTQLAFDSASFVSGAA
GIGAGLIGASTTAAVLGGAGVILGGLAVGFTALAQAFGAVAEDAKAVGRY
FDTLDKAYQGNGYRYDEKQQVLVPLAGAVVKRLDLRSNEVGFDSQYIYRT
HHGSTGSGAINYFFWVGDFPRMIHDRAQAIEVRSGIGHGAKPPRLDHGDS
RTVILPGTPKSYISYEYMILPGATTRHDTGFDVIRKLEQDRRFDYDFYIF
PSEETIRRIHQEYVETPVEVLLDGHNRQLVVPQLPKELYGYLRYDIQGAG
GEYLIGLNEGTEVRLSNEAGRQPSRWIIDSSQLESDSITVAKDHLLVGGV
KVRLDPAQSGQVLLVNAKGEVRAADFAGQTTYVVKEDASQWQVSGQRIEQ
HLKELAQAHQLHGQYVVVENYKHGERNVGRAYYEVAKDRMLFTDTDVQQA
RNAQLGAVIGEHAYFVDAENAAAWRVDIASGKVDAQFAPAFNQSAGQISR
FWQEGDAVYLARRYQLKEREAELSFRILGDRMELVGVVGDESLLQLSASN
SQHGKDAKTLLNTLLKGYETQATQRDTPVYSLGAPVLEPTAAELITVFGL
DNAKVAHRYWVRSSDGIVIKPNLAPPAGQAPRADAPGQAQSAWQIPADLV
LAGSQAQPGGQEVFYFYSKAQQVLFRQEGPGQKVLDAGQPSALRLSTPPL
ANVLNLNGHLLAVTNDGRMARIEATGRLSYEAVNEHWLKAHSNWWKNLAE
VAGSNATLAVFGVKAADGKSALPVWYHNGQVVVASSALQGKPLQFLGFDS
ASASARLFEPESGKLYLQPPLTAQALATAFGKDEVLEASAQLPAAIDWMP
KQPLRSAVQVDAGLRLTTVQGEVLLRSNNGDVQLVAVDKGWQQAHLGNLP
QALATVAGQWGAKGVLSLQDGDTRGWFDIASGQMFASNGIPGGSDLRFIG
VAAGTPNSAYVYSPTAQALYQVKDGKALQLGHYANVERIGSSLLLQGASG
NAPQDDLAPPLIAGVDSVVLHGGAGDDTYRFSPAMWAHYRSVVIDNDDPG
LALDRVILPVADGKNILVSRRGEDVQLTDTGNGTALVLRQVLGSQAAAHG
HLLIELKGDSSMISVEQLLKGFGPSGSAGDSVFELAWSQRETLPAANALS
SAADVPDSAADGRGPSLAKLSGAMAAFADTGGAREQLPKNHQAAQAVLVP
SLT.

The SEQ ID No. 1 is annotated as cytolysin FitD.

The cytolysin FitD from CL145A (SEQ ID No. 1) can be cloned and expressed in a non-toxic host for molluscicidal activity and to generate active protein to determine specific activity in the CL145A cell via mussel bioassay. A gene knockout of the active strain can also reveal the presence of other mussel/insect toxins.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for controlling mussels in a liquid location comprising:
   administering an effective amount of a composition having
   (a) a protein that is 100% identical to SEQ ID NO:1, and
   (b) gamma-dodecalactone, delta-tridecalactone, piliferolide A, alpha-heptyl-gamma-butyrolactone and/or 11-hydroxy-12-ene-octadecanoic acid,
   to control said mussels at said liquid location.

2. The method according to claim 1, wherein said liquid location is in a pipe, a body of water or paint.

3. The method according to claim 1, wherein said composition further comprises an inert material.

4. A composition for controlling mussels in a liquid location comprising:
   an effective amount of a composition having
   (a) a protein that is 100% identical to SEQ ID NO:1, and
   (b) gamma-dodecalactone, delta-tridecalactone, piliferolide A, alpha-heptyl-gamma-butyrolactone and/or 11-hydroxy-12-ene-octadecanoic acid,
   to control said mussels at said liquid location.

5. The composition according to claim 4, wherein said composition further comprises an inert material.

* * * * *